United States Patent [19]

Cragoe, Jr. et al.

[11] 4,246,406

[45] Jan. 20, 1981

[54] HETEROCYCLIC SUBSTITUTED PYRAZINOYLGUANIDINES

[75] Inventors: Edward J. Cragoe, Jr., Lansdale; Otto W. Woltersdorf, Jr., Chalfont; Susan J. DeSolms, Norristown, all of Pa.

[73] Assignee: Merck & Co., Inc., Rahway, N.J.

[21] Appl. No.: 24,293

[22] Filed: Mar. 27, 1979

[51] Int. Cl.$^3$ .................. C07D 279/06; C07D 241/02; A61K 31/54; A61K 31/495
[52] U.S. Cl. ...................... 544/54; 544/58.6; 544/405; 544/407; 424/246; 424/250
[58] Field of Search .................. 544/54, 58, 405, 58.6, 544/407; 424/246, 250

[56] References Cited

U.S. PATENT DOCUMENTS 3,328,404   6/1967   Pollak et al. .................. 544/405

*Primary Examiner*—Henry R. Jiles
*Assistant Examiner*—Robert C. Whittenbaugh
*Attorney, Agent, or Firm*—Michael C. Sudol, Jr.; Harry E. Westlake

[57] ABSTRACT

The case involves novel heterocyclic substituted pyrazinoylguanidines and a process for preparing same. The heterocyclic pyrazinoylguanidines are eukalemic agents possessing diuretic and natriuretic properties.

8 Claims, No Drawings

HETEROCYCLIC SUBSTITUTED PYRAZINOYLGUANIDINES

SUMMARY OF THE INVENTION

The instant case covers novel heterocyclic substituted pyrazinoylguanidine compounds and a process for making the same. The novel pyrazinecarboxamides of this invention are depicted in Formula I below.

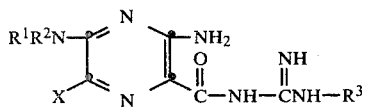

wherein $R^1$ is hydrogen or lower alkyl having from 1 to 5 carbon atoms such as methyl, ethyl, isopropyl, n-butyl, n-pentyl, $R^2$ is hydrogen, lower alkyl having from 1 to 5 carbon atoms such as methyl, ethyl, isopropyl and n-pentyl, $R^3$ is a 5 or 6 membered heterocyclic ring containing from 1 to 3 heterocyclic atoms selected from the elements N, O or S, said ring containing from 0 to 2 substituents selected from lower alkyl having 1 to 5 carbon atoms, halo, oxy or hydroxy.

X is halogen such as chloro, bromo, fluoro or iodo, and the pharmaceutically acceptable non-toxic acid addition salts thereof.

The preferred compounds of this invention, in other words, those having enhanced diuretic, saluretic activity while maintaining unchanged potassium blood levels are those compounds of Formula I wherein $R^1$ is hydrogen, $R^2$ is hydrogen, or lower alkyl having from 1 to 3 carbon atoms but particularly isopropyl, $R^3$ is as previously defined; X is chloro and the pharmaceutically acceptable non-toxic acid addition salts thereof.

Particular definitions of $R^3$ can be

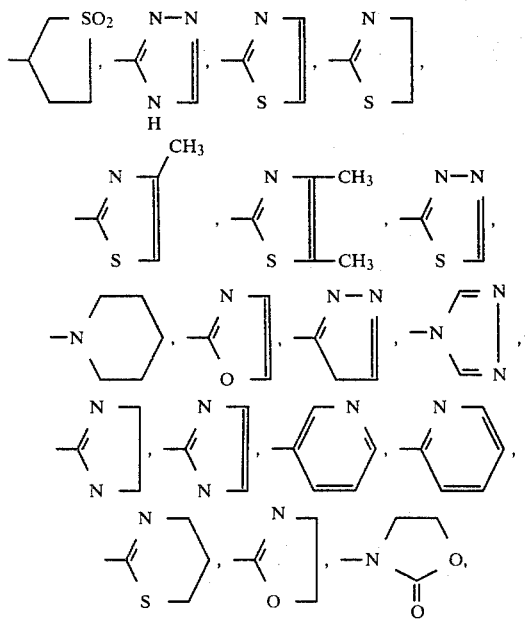

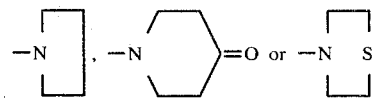

Specifically preferred compounds of this invention are as follows:

3,5-diamino-6-chloro-N-[(2-thiazolinylamino)aminomethylene]-2-pyrazinecarboxamide;

3,5-diamino-N-[(2-thiazolylamino)aminomethylene]-6-chloro-2-pyrazinecarboxamide;

3-amino-6-chloro-5-isopropylamino-N-[(2-thiazolinylamino)aminomethylene]-2-pyrazinecarboxamide;

3,5-diamino-6-chloro-N-[(2-oxazolinylamino)aminomethylene]-2-pyrazinecarboxamide;

3,5-diamino-6-chloro-N-{[2-(4,5-dihydro)-thiazinylamino]aminomethylene}-2-pyrazinecarboxamide hydrochloride hemihydrate.

The compounds of this invention as shown by Formula I and the preferred compounds discussed above are useful because they possess diuretic and natriuretic properties. In addition, they are useful eukalemic saluretics, in other words, the compounds of the instant case cause neither loss or abnormal retention of potassium ions. Other well known diuretics such as furosemide, chlorthalidone and acetazolamide cause an increase in potassium excretion which often results in muscular weakness. Thus, the compounds of this invention maintain the excretion of potassium at approximately normal levels while causing an increased renal elimination of sodium ions and water which is the desirable characteristic of the diuretic.

Also covered within the scope of the above Formula I compounds and the preferred compounds are the pharmaceutically acceptable acid addition salts thereof. These salts can be made by reacting the free base with a pharmaceutically acceptable acid such as for example, hydrochloric acid, sulfuric acid, hydrobromic acid or isethionic acid. These salts, as stated above, are to be considered as included in this invention.

The products of this invention can be administered to patients (both human and animal) in the form of pills, tablets, capsules, elixirs, injectable preparations and the like. They can be administered either orally or parentally or any other feasible method as known to those skilled in the art such as intravenously or in the form of suppositories and the like.

The type of formulation to be administered can be comprised of one or more of the compounds of this invention as the only essential active ingredient of the pharmaceutical formulation. The formulations are merely combinations of the active ingredient mentioned with pharmaceutically inert carriers and the like. Several pharmaceutical formulations are prepared as shown in Example 27.

The compounds of this invention are advantageously administered at a dosage range of from about 5 mg. to about one gram per day or a somewhat higher or lower dosage at the physician's discretion, preferably in subdivided amounts on a 2 to 4 times a day regimen and most preferably at a dosage range from 10 to 500 mg. per day. It will be realized by those skilled in the art that the dosage range for any particular patient (animal or human) will depend upon the severity of the disease treated, weight of the patient and any other condition which the physician or other person skilled in the art will take account of.

The compounds disclosed in this invention in Formula I and the preferred compounds can be formed according to either of the two processes described herein. The first process can be depicted by the following equation:

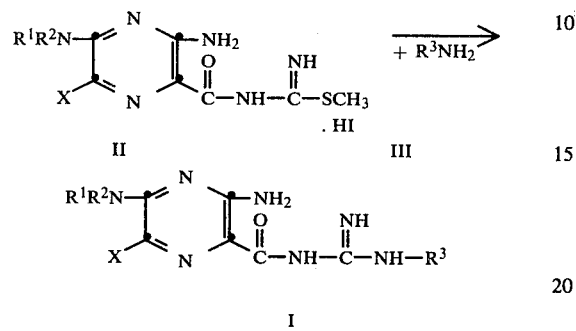

involving a reaction of a pseudothiourea compound II with a substituted amine III to produce the desired product.

A pseudothiourea (Compound II) is reacted with an amine (III) to yield the desired compounds of Formula I. This reaction is preferably carried out in an inert solvent such as, for example, tetrahydrofuran, 1,2-dimethoxyethane or bis(2-methoxyethyl)ether if the amine compound III is a solid or without solvent if the amine compound III is a liquid. The reaction is best carried out in a mole ratio of 1 to 4 moles of the amine Compound III to one mole of the pseudothiourea Compound II. The reaction is preferably carried out at a temperature of from 25° C. to the reflux temperature of the particular solvent used. It is also carried out for a time of 1 to 48 hours. The latter conditions of temperature and time, however, are not critical to the reaction and can be adjusted by those skilled in the art. The product which can be isolated from the reaction mixture by methods known in the art generally by, for example, adding crushed ice to the reaction mixture to precipitate the desired compounds I. Detailed descriptions of this process are contained in the Examples. One can prepare the pseudothiourea compounds according to the following reaction scheme which starts with the known pyrazinoate IV.

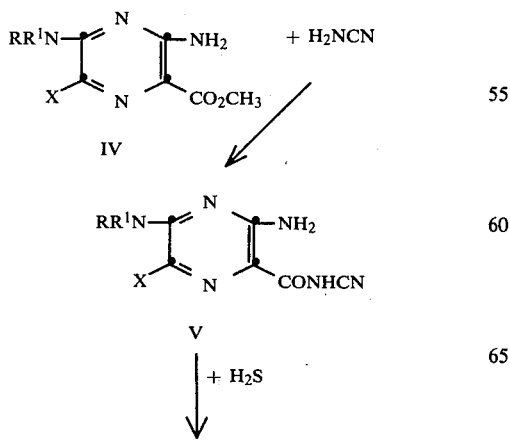

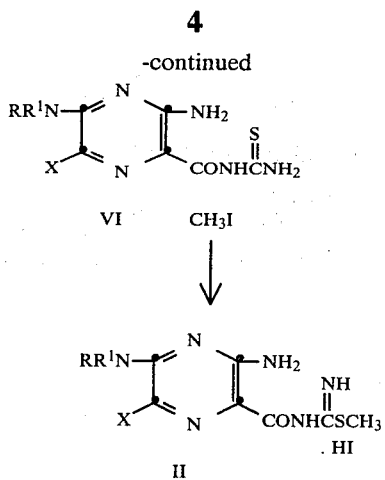

In the preparation of the pseudothiourea Compound II, one can begin by reacting the pyrazinoate IV with cyanamide and sodium methoxide to yield an intermediate cyanamide compound, V, which is then reacted with hydrogen sulfide to yield a thiourea compound VI. This thiourea Compound VI is then reacted with methyl iodide to yield the desired pseudothiourea starting material II. As stated previously Compound IV is known in the art, such as for example from U.S. Pat. Nos. 3,313,813 and 4,087,526.

A second reaction for forming the end product starts by reacting a pyrazinoic acid VII with carbonyl diimidazole to form an active acylating agent VIII (not isolated) which intermediate is then reacted with a substituted guanidine IX to yield the desired product. This is depicted in the following equation:

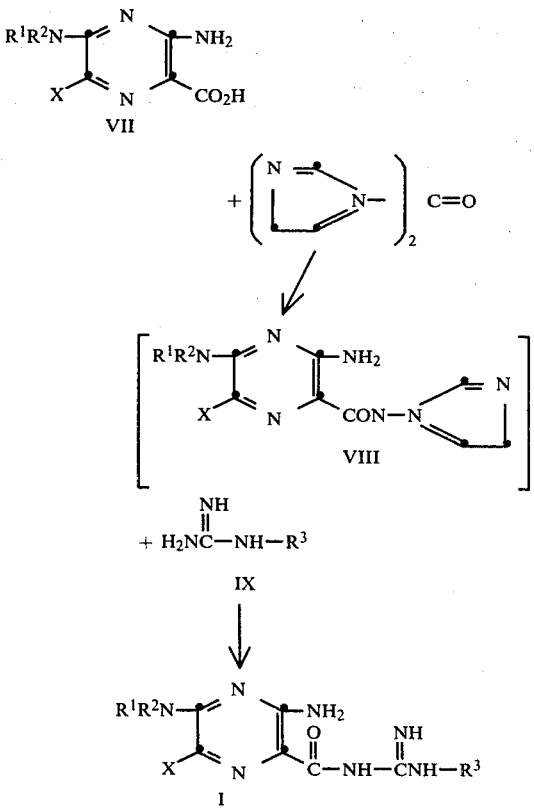

In this process a pyrazinoic acid VII is reacted with carbonyldiimidazole to yield an active acylating agent VIII which is not isolated. This portion of the reaction is carried out in an organic solvent such as dimethylformamide at about 10° C. to 40° and for a time of 1 to 8 hours. The reaction mixture is then treated with an aqueous solution of the substituted guanidine IX at a temperature of about 25° C. to 100° C. for a time of from 1 to 48 hours. The desired product I is then isolated from the reaction mixture by known methods such as by adding water to precipitate the product I.

In both processes described above $R^1$, $R^2$, $R^3$ and X are as defined for the compounds of Formula I.

All the starting materials used in the two processes described above are shown in and disclosed in U.S. Pat. No. 3,313,813 mentioned previously or at least can be obviously prepared from compounds disclosed in the aforementioned patent. The preparation of those not shown in U.S. Pat. No. 3,313,813 and which are not obviously prepared therefrom is shown in the Examples.

EXAMPLE 1

1-(3-Amino-5-isopropylamino-6-chloropyrazinoyl)-2-methyl-2-thiopseudourea hydroiodide

Step A:

(2-Amino-5-isopropylamino-6-chloropyrazinoyl)cyanamide

To a solution of sodium methoxide (19.0 g., 0.35 mole) in methanol (300 ml.) is added cyanamide (15 g., 0.36 mole) and methyl 3-amino-5-isopropylamino-6-chloropyrazinoate (29 g., 0.118 mole). The reaction mixture is refluxed overnight, evaporated at reduced pressure to ½ volume, added to ice (100 g.) and neutralized with acetic acid to give (2-amino-5-isopropylamino-6-chloropyrazinoyl)cyanamide which melts at 232° C. with decomposition after recrystallization from isopropanol.

Elemental analysis for $C_9H_{11}ClN_6O$: Calc: C, 42.44; H, 4.35; N, 3300; Found: C, 42.52; H, 4.36; N, 33.25.

Step B:

(3-Amino-5-isopropylamino-6-chloropyrazinoyl)thiourea

To a stirred solution of (3-amino-5-isopropylamino-6-chloropyrazinoyl)cyanamide (6.0 g., 0.0235 mole) in pyridine (40 ml) is added triethylamine (4 ml.). The reaction mixture is heated on a steam bath for 1½ hours while a slow stream of hydrogen sulfide gas is bubbled into the solution. The reaction mixture is cooled and added to ice-water to give 6 g. of (3-amino-5-isopropylamino-6-chloropyrazinoyl)thiourea which melts at 195° C. after recrystallization from ethanol.

Elemental analysis for $C_9H_{13}ClN_6OS$: Calc.: C, 37.43; H, 4.54; N, 29.11; Found: C, 37.45; H, 4.54; N, 29.31.

Step C:

1-(3-Amino-5-isopropylamino-6-chloropyrazinoyl)-2-methyl-2-thiopseudourea hydroiodide A solution of (3-amino-5-isopropylamino-6-chloropyrazinoyl)thiourea (6.0 g.) and methyl iodide (15 ml) in acetone (60 ml.) is refluxed for 1½ hours and cooled in an ice bath to give 8.7 g. of 1-(3-amino-5-isopropylamino-6-chloropyrazinoyl)-2-methyl-2-thiopseudourea hydroiodide which melts at 185° C.

EXAMPLE 2

1-(3-Amino-5-dimethylamino-6-chloropyrazinoyl)-2-methyl-2-thiopseudourea hydroiodide A solution of (3-amino-5-dimethylamino-6-chloropyrazinoyl)thiourea (2.0 g.) and methyl iodide (5 ml.) in acetone (60 ml.) is heated at reflux for ½ hour during which time the 1-(3-amino-5-dimethylamino-6-chloropyrazinoyl)-2-methyl-2-thiopseudourea hydroiodide precipitates, m.p. 195° C.

Elemental analysis for $C_9H_{13}ClN_6OS.HI$ Calc.: C, 25.94; H, 3.39; N, 20.17; Found: C, 26.13; H, 3.31; N, 20.50.

EXAMPLE 3

1-(3,5-Diamino-6-chloropyrazinoyl)-2-methyl-2-thiopseudourea hydroiodide

A solution of (3,5-diamino-6-chloropyrazinoyl)thiourea (1.0 g.) and methyl iodide (4 ml.) in acetone (100 ml.) is heated at reflux for one hour during which time the 1-(3,5-diamino-6-chloropyrazinoyl)-2-methyl-2-thiopseudourea hydroiodide precipitates m.p. 222° C. with decomposition.

Elemental analysis for $C_7H_9ClN_6OS.HI$; Calc.: C, 21.63; H, 2.59; N, 21.63; Found: C, 21.97; H, 2.68; N, 21.50.

EXAMPLE 4

Preparation of 3,5-Diamino-6-chloro-N-[(3-pyridylamino)aminomethylene]-2-pyrazinecarboxamide hemihydrate 1-(3,5-Diamino-6-chloropyrazinoyl)-2-methyl-2-thiopseudourea hydroiodide (970 mg., 0.0025 mole) is added to a solution of 3-aminopyridine (940 mg., 0.01 mole) in dry tetrahydrofuran (20 ml.) and the mixture is heated at reflux for 2 hours, then added to crushed ice-water (200 ml.) to precipitate 423 mg. of 3,5-diamino-6-chloro-N-[(3-pyridylamino)aminomethylene]2-pyrazinecarboxamide hemihydrate, m.p. 220°-2° C.

Elemental analysis for $C_{11}H_{11}ClN_8O.\frac{1}{2}H_2O$: Calc.: C, 41.85; H, 3.83; N, 35.49; Cl, 11.23; Found: C, 41.37; H, 3.91; N, 35.58; Cl, 11.58.

| Ex. | Pseudothiourea | Substituted Amine | Solvent | End Product and Analysis |
|---|---|---|---|---|
| 5 | 1-(3,5-diamino-6-chloropyrazinoyl)-2-methyl-2-thio-pseudourea . HI (9.7 g., 0.025 mole) | 3-amino-1,2,4-triazole (8.4 g., 0.1 mole) | Tetrahydrofuran (250 ml.) | 3,5-diamino-6-chloro-N-[3-[1,2,4-triazolyl]amino)aminomethylene]-2-pyrazinecarboxamide hemihydrate (2.75 g.) Melting point: >300° C. $C_8H_9ClN_{10}O . \frac{1}{2} H_2O$: Calc.: C, 31.43; H, 3.30; Cl, 11.60; |

-continued

| Ex. | Pseudothiourea | Substituted Amine | Solvent | End Product and Analysis |
|---|---|---|---|---|
| | | | | Found: C, 31.68; H, 3.07; Cl, 11.94. |
| 6 | 1-(3,5-diamino-6-chloropyrazinoyl)-2-methyl-2-thio-pseudourea . HI (3.88 g., 0.01 mole) | 3-aminopyrazole (3.32 g., 0.04 mole) | tetrahydrofuran (50 ml.) | 3,5-diamino-N-[(3-pyrazolylamino)-aminomethylene]-6-chloro-2-pyrazinecarboxamide hemihydrate (2.62 g.) Melting point: 224° C. $C_9H_{10}ClN_9O \cdot \frac{1}{2} H_2O$ Calc.: C, 35.48; H, 3.64; N, 41.37; Found: C, 35.32; H, 3.52; N, 41.32 |
| 7 | 1-(3,5-diamino-6-chloropyrazinol)-2-methyl-2-thio-pseudourea . HI 3.88 g., 0.01 mole) | 2-amino-4-methyl thiazole (3.42 g., 0.03 mole) | tetrahydrofuran (100 ml.) | 3,5-diamino-N-[2-(4-methyl)-thiazolylamino]aminomethylene-6-chloro-2-pyrazinecarbox-amide (1.0 g.) Melting point: 258–60° C. $C_{10}H_{11}ClN_8OS$: Calc: C, 36.76; H, 3.39; N, 34.29; Found: C, 36.76; H, 3.28, N, 34.28. |
| 8 | 1-(3,5-diamino-6-chloropyrazinoyl)-2-methyl-2-thio-pseudourea . HI (5.82 g., 0.015 mole) | 2-amino-2-thiazoline (6.12 g., 0.06 mole) | bis(2-methoxy-ethyl)ether (100 ml.) | 3,5-diamino-6-chloro-N-[(2-thiazolinylamino)aminomethylene]-2-pyrazinecarboxamide (1.56 g.) Melting point: 241–3° C. $C_9H_{11}ClN_8OS$: Calc.: C, 34.34; H, 3.52; N, 35.60; Found: C, 34.34; H, 3.43; N, 35.12. |
| 9 | 1-(3,5-diamino-6-chloropyrazinoyl)-2-methyl-2-thio pseudourea . HI (3.58 g., 0.01 mole) | 2-amino-thiazole (4.00 g., 0.04 mole) | tetrahydrofuran (100 ml.) | 3,5-diamino-N-[(2-thiazolylamino)-aminomethylene]-6-chloro-2-pyrazinecarboxamide (1.12 g.) Melting point: 229–31° C. $C_9H_9ClN_8OS$: Calc.: C, 34.57; H, 2.90; N, 35.83; Found: C, 34.10; H, 2.85; N, 35.66 |
| 10 | 1-(3,5-diamino-6-chloropyrazinoyl)-2-methyl-2-thio-pseudourea . HI (1.94 g., 0.005 mole) | 4-amino-1,2,4-triazole (1.68 g., 0.02 mole) | bis(2-methoxy-ethyl)ether (25 ml.) | 3,5-diamino-N-[(1,2,4-triazol-4-ylamino)aminomethylene]-6-chloro-2-pyrazinecarbox-amide hemihydrate (920 mg.) Melting point: 275–7° C. $C_8H_9ClN_{10}O \cdot \frac{1}{2} H_2O$: Calc.: C, 31.43; H, 3.30; N, 45.82; Found; C, 31.60; H, 2.90; N, 45.38. |
| 11 | 1-(3,5-diamino-6-chloropyrazinoyl)-2-methyl-2-thio pseudourea . HI (1.94 g., 0.005 mole) | 2-amino-pyridine (4.70 g., 0.05 mole) | none | 3,5-diamino-N-[(2-pyridylamino)-aminomethylene]-6-chloro-2-pyrazinecarboxamide . $\frac{1}{4}$ $H_2O$ (350 mg.) Melting point: 218–220° C. $C_{11}H_{11}ClN_8O \cdot \frac{1}{4} H_2O$: Calc.: C, 42.45; H, 3.72; N, 36.01; Cl, 11.39; Found: C, 42.40; H, 3.58; N, 35.86; Cl, 11.61. |
| 12 | 1-(3,5-diamino-6-chloropyrazinoyl)-2-methyl-2-thio-pseudourea . HI (3.88 g., 0.01 mole) | N-aminopiperidine (10 ml.) | none | 3,5-diamino-N-[(piperidin-1-yl-amino)aminomethylene]-6-chloro-2-pyrazinecarboxamide (1.45 g) Melting point: 137–9° C. $C_{11}H_{17}ClN_8O$: Calc.: C, 43.17; H, 6.19; N, 32.48; Found: C, 42.96; H, 6.23; N, 32.49 |
| 13 | 1-(3-amino-6-chloro-5-dimethyl-aminopyrazinoyl)-2-methyl-2-thio pseudourea . HI (2.2 g., 0.0053 mole) | 2-aminothiazoline (2.04 g., 0.02 mole) | bis(2-methoxy-ethyl)ether (20 ml.) | 3-amino-6-chloro-5-di-methylamino-N-[(2-thia-zolinylmino)aminomethyl-ene]-2-pyrazinecarbox-amide (340 mg.) Melting point: 221–4° C. $C_{11}H_{15}ClN_8OS$: Calc.: C, 38.54; H, 4.41; N, 32.69; Found: C, 38.88; H, 4.44; N, 32.82. |
| 14 | 1-(3-amino-6-chloro-5-isopropylamino-pyrazinoyl)-2-methyl-2-thiopseudourea | 2-amino-thiazoline (3.06 g., 0.03 mole) | bis(2-methoxy-ethyl)ether (50 ml.) | 3-amino-6-chloro-5-isopropyl-amino-N-[(2-thiazolinylamino)-aminomethylene]-2-pyrazine-carboxamide (650 mg.) |

| Ex. | Pseudothiourea | Substituted Amine | Solvent | End Product and Analysis |
|---|---|---|---|---|
| | hydroiodide (4.3 g., 0.01 mole) | | | Melting point: 210–12° C. $C_{12}H_{17}ClN_8OS$: Calc.: C, 40.39; H, 4.81; N, 31.40; Cl, 9.94; Found: C, 40.18; H, 4.74; N, 30.84; Cl, 9.59. |
| 15 | 1-(3,5-diamino-6-chloropyrazinoyl)-2-methyl-2-thio-pseudourea . HI | 2-amino-oxazoline | bis(2-methoxy-ethyl)ether | 3,5-diamino-6-chloro-N-[(2-oxazolinylamino)amino-methylene]-2-pyrazinecarbox-amide Melting point: 199–200° C. $C_9H_{11}ClN_8O_2$: Calc.: C, 36.19; H, 3.71; N, 37.51; Found: C, 36.25; H, 3.65; N, 37.23. |

EXAMPLE 16

Preparation of 3,5-Diamino-6-chloro-N-[(4-thiomorpholinyl)aminomethylene]-2-pyrazinecarboxamide Thiomorpholine hydrochloride (2.10 g., 0.015 mole), triethylamine (2.1 ml., 0.015 mole), and 1-(3,5-diamino-6-chloropyrazinoyl)-2-methyl-2-thiopseudourea hydroiodide (1.94 g., 0.005 mole) are heated in tetrahydrofuran (50 ml.) at reflux for 4 hrs. The reaction mixture is added to ice-water to precipitate 590 mg. of 3,5-diamino-6-chloro-N-[(4-thiomorpholinyl)aminomethylene]-2-pyrazinecarboxamide which melts at 234°-6° C. after reprecipitation from dilute hydrochloric acid with sodium hydroxide.

Elemental analysis for $C_{10}H_{14}ClN_7OS$: Calc.: C, 38.04; H, 4.47; N, 31.05; Found: C, 37.91; H, 4.46; N, 31.21.

Following the procedure of Example 16 but substituting the following amounts of major reactants in place of the corresponding reactants of Example 16, there is obtained the appropriate listed end product.

EXAMPLE 19

Preparation of 3,5-Diamino-6-chloro-N-[(1,1-dioxotetrahydrothien-3-ylamino)aminomethylene]-2-pyrazinecarboxamide monohydrate 3-Amino-1,1-dioxotetrahydrothiophene hydrochloride (17.1 g., 0.1 mole) is added to a solution of sodium methoxide (5.4 g., 0.1 mole) in methanol (150 ml.) with stirring at 25° C. After 0.5 hr. the sodium chloride is filtered off and the filtrate concentrated to dryness leaving the free amine residue which is suspended in tetrahydrofuran (250 ml.). 1-(3,5-Diamino-6-chloropyrazinoyl)-2-methyl-2-thiopseudourea hydroiodide (9.7 g., 0.025 mole) is added and the mixture heated at reflux for 2 hrs., the product filtered then dissolved in hot water and treated with 10 N sodium hydroxide solution to precipitate 5.33 g. of 3,5-diamino-6-chloro-N-[(1,1-dioxotetrahydrothien-3-ylamino)aminomethylene]-2-pyrazinecarboxamide monohydrate. m.p. 193°-5° C.

Elemental analysis for $C_{10}H_{14}ClN_7O_3S.H_2O$: Calc.: C, 32.84; H, 4.41; N, 26.80; Found: C, 33.26; H, 4.09; N, 27.03.

Following the procedure of Example 19 but substituting the following amounts of major reactants in place of the corresponding reactants of Example 19 there is obtained the appropriate listed end product.

| Ex. | Pseudothiourea | Substituted Amine | Solvent | | End Product and Analysis |
|---|---|---|---|---|---|
| 17 | 1-(3,5-diamino-6-chloropyrazinoyl)-2-methyl-2-thio-pseudourea . HI (3.88 g., 0.01 mole) | 2-amino-1,3,4-thiadiazole hydrochloride (4.14 g., 0.03 mole) | bis(2-meth-oxyethyl)ether (50 ml.) | $Et_3N$ (4.2 ml, 0.03 mole) | 3,5-diamino-N-{[2-(1,3,4-thiadiazolyl)amino]amino-methylene}-6-chloro-2-pyrazinecarboxamide (510 mg.) Melting point: 297° C. $C_8H_8ClN_9OS$: Calc.: C, 31.33; H, 2.84; N, 39.40; Found C, 31.34; H, 2.72; N, 39.24. |
| 18 | 1-(3,5-diamino-6-chloropyrazinoyl)-2-methyl-2-thio-pseudourea . HI (3.38 g., 0.01 mole) | N-aminopyrrol-idine hydro-chloride (2.61 g., 0.03 mole) | tetrahydro furan (100 ml.) | $Et_3N$ (4.2 ml, 0.03 mole) | 3,5-diamino-6-chloro-N-[(pyrrolidin-1-ylamino)-aminomethylene]-2-pyrazine-carboxamide (960 mg) Melting point: 106–9° C. $C_{10}H_{15}ClN_8O$: Calc.: C, 40.21; H, 5.06; N, 37.51; Found: C, 40.58; H, 5.12; N, 37.08 |

| Ex. | Pseudothiourea | Substituted Amine | NaOCH₃ | End Product and Analysis |
|---|---|---|---|---|
| 20 | 1-(3,5-diamino-6-chloropyrazinoyl)-2-methyl-2-thio-pseudourea . HI (1.94 g., 0.005 mole) | 4-piperidone monohydrate hydrochloride (3.07 g., 0.02 mole) | (1.08 g., 0.02 mole) | 3,5-diamino-6-chloro-N-[(4-oxo-piperidinyl)aminomethylene]-2-pyrazinecarboxamide hemihydrate (380 mg.) Melting point: 244–7° C. $C_{11}H_{14}ClN_7O_2 . \frac{1}{2} H_2O$: Calc.: C, 41.19; H, 4.71; N, 30.57; Cl, 11.05; Found: C, 40.58; H, 4.39; N, 30.69; Cl, 11.43. |
| 21 | 1-(3,5-diamino-6-chloropyrazinoyl)-2-methyl-2-thio-pseudourea . HI (3.88 g., 0.01 mole) | 2-amino-4,5-di-methylthiazole hydrobromide (6.27 g., 0.03 mole) | (1.62 g., 0.03 mole) | 3,5-diamino-N-{[2-(4,5-dimethyl)-thiazoylamino]aminomethylene}-6-chloro-2-pyrazinecarboxamide (1.92 g.) Melting point: 264–6° C. $C_{11}H_{13}ClN_8OS$: Calc.: C, 38.77; H, 3.85; N, 32.88; Found: C, 38.68; H, 3.85; N, 32.99 |
| 22 | 1-(3,5-diamino-6-chloropyrazinoyl)-2-methyl-2-thio-pseudourea . HI (3.88 g., 0.01 mole) | 2-amino-5,6-di-hydro-4H-1,3-thiazine hydrochloride (4.59 g., 0.03 mole) | (1.62 g., 0.03 mole) | 3,5-diamino-6-chloro-N-{[2-(4,5-dihydro)thiozinylamino]amino-methylene}-2-pyrazinecarbox-amide hydrochloride hemihydrate (271 g.) Melting point: 253–4° C. $C_{10}H_{13}ClN_8OS . HCl . \frac{1}{2} H_2O$; Calc.: C, 32.09; H, 4.04; N, 29.94; Found: C, 32.00; H, 3.99; N, 30.27. |

EXAMPLE 23

Preparation of 3,5-Diamino-6-chloro-N-{[3-(2-oxoöxazolidinyl-)amino]aminomethylene}-2-pyrazinecarboxamide 1-(3,5-Diamino-6-chloropyrazinoyl)-2-methyl-2-thiopseudourea hydroiodide (2.23 g., 0.005 mole) is added to a solution of 3-amino-2-oxazolidinone (2.04 g., 0.02 mole) in dry methanol (100 ml.) with stirring at 25° C. under $N_2$. After 20 hours the solid precipitate is removed, dissolved in $H_2O$, then treated with 15 N ammonium hydroxide to give 950 mg. of 3,5-diamino-6-chloro-N-{[3-(2-oxoöxazolidinyl)amino]aminomethylene}-2-pyrazine=carboxamide, m.p. 281°-3° C.

Elemental analysis for $C_9H_{11}ClN_8O_3$: Calc.: C, 34.35; H, 3.52; N, 35.61; Found: C, 34.15; H, 3.60; N, 35.21.

EXAMPLE 24

3,5-Diamino-6-chloro-N-[(2-oxazolinylamino)aminomethylene]-2-pyrazinecarbox-amide.¾ $H_2O$ N,N'-Carbonyldiimidazole (1.62 g., 0.01 mole) is added to a solution of 3,5-diamino-6-chloropyrazinoic acid (1.89 g., 0.01 mole) in dry dimethylformamide (80 ml.) at 25° C. under $N_2$. After 1 hour the 1-(3,5-diamino-6-chloro-2-pyrazinoyl)imidazole formed is not isolated but is treated in situ with 2-guanidinooxazoline sulfate (3.54 g., 0.02 mole) dissolved in $H_2O$ (15 ml.) −10 N NaOH solution (2 ml.). After stirring at 55° C. for 20 hours, removing the insoluble solid, azetroping most of the DMF with p-xylene, then adding the residue to $H_2O$, there is obtained 460 mg. of 3,5-diamino-6-chloro-N-[(2-oxazolinylamino)aminomethylene]-2-pyrazinecarboxamide.¾ $H_2O$ which melts at 199°–200° C. after reprecipitation from dil. HCl with NH₄OH.

Elemental analysis for $C_9H_{11}ClN_8O_2$: Calc.: C, 36.19; H, 3.71; N, 37.51; Found: C, 36.25; H, 3.65; N, 37.23.

EXAMPLE 25

3,5-Diamino-6-chloro-N-[(2-imidazolylamino)aminomethylene]-2-pyrazinecarboxamide N,N'-Carbonyldiimidazole (1.62 g., 0.01 mole) is added to a solution of 3,5-diamino-6-chloropyrazinoic acid (1.89 g., 0.01 mole) in dry dimethylformamide (80 ml.) at 25° C. under $N_2$. After 1 hour the 1-(3,5-diamino-6-chloro-2-pyrazinoyl)imidazole formed is not isolated, but is treated in situ with 2-guanidinoimidazole dihydrochloride (3.96 g., 0.02 mole) dissolved in $H_2O$ (15 ml.) −10 N NaOH solution (2 ml.). After stirring at 55° C. for 20 hours, removing the insoluble solid, azetroping most of the DMF with p-xylene, then adding the residue to $H_2O$, there is obtained 3,5-diamino-6-chloro-N-[(2-imidazolylamino)aminomethylene]-2-pyrazinecarboxamide.

EXAMPLE 26

3,5-Diamino-6-chloro-N-[(2-imidazolinylamino)aminomethylene]-2-pyrazinecarboxamide N,N'-Carbonyldiimidazole (1.62 g., 0.01 mole) is added to a solution of 3,5-diamino-6-chloropyrazinoic acid (1.89 g., 0.01 mole) in dry dimethylformamide (80 ml.) at 25° C. under $N_2$. After 1 hour the 1-(3,5-diamino-6-chloro-2-pyrazinoyl)imidazole formed is not isolated, but is treated in situ with 2-guanidinoimidazoline (2.54 g., 0.02 mole) dissolved in $H_2O$ (15 ml.) −10 N NaOH solution (2 ml.). After stirring at 55° C. for 20 hours, removing the insoluble solid, azetroping most of the DMF with p-xylene, then adding the residue to $H_2O$, there is obtained 3,5-diamino-6-chloro-N-[(2-imidazolinylamino)aminomethylene]-2-pyrazinecarboxamide.

EXAMPLE 27

Compressed Tablet containing 50 mg. of active ingredient.

| | Per tablet, Mg. |
|---|---|
| 3,5-diamino-6-chloro-N-[(2-thiazolinylamino)aminomethylene]-2-pyrazinecarboxamide | 50 |
| Calcium phosphate dibasic | 200 |
| Ethyl cellulose (as 5% solution in ethanol) | 5 |
| Unmixed granulation | 255 |
| Add: | |
| Starch, corn | 14 |
| Magnesium stearate | 1 |
| | 270 |

Directions

Mix the active ingredient above and calcium phosphate and reduce to a No. 60 mesh powder. Granulate with Ethocel in alcohol and pass the wet granulation through a No. 10 screen. Dry the granulation at 110° F. for 12–18 hours. Dry grind to a No. 20 mesh. Incorporate the "adds" and compress into tablets each weighing 270 mg.

What is claimed is:

1. A compound of the formula:

wherein
- R¹ is hydrogen, lower alkyl having from 1 to 5 carbon atoms;
- R² is hydrogen, lower alkyl having 1 to 5 carbon atoms;
- R³ is a 5 or 6 membered heterocyclic ring containing from 1 to 3 heterocyclic atoms selected from the elements N, O or S, said ring containing from 0 to 2 substituents selected from lower alkyl having 1 to 5 carbon atoms, halo, oxy or hydroxy;
- X is halo, and the pharmaceutically acceptable non-toxic acid addition salts thereof.

2. A compound of the formula:

wherein
- R¹ is hydrogen;
- R² is hydrogen or lower alkyl having from 1 to 3 carbon atoms;
- R³ is a 5 or 6 membered heterocyclic ring containing from 1 to 3 heterocyclic atoms selected from the elements N, O or S, said ring containing from 0 to 2 substituents selected from lower alkyl having 1 to 5 carbon atoms, halo, oxy or hydroxy and the pharmaceutically acceptable non-toxic acid addition salts thereof.

3. A compound of claim 1 wherein R³ is

4. A compound of claim 2 wherein
- R¹ is hydrogen;
- R² is hydrogen;
- R³ is to yield 3,5-diamino-6-chloro-N-[(2-thiazolinylamino)aminomethylene]-2-pyrazinecarboxamide.

5. A compound of claim 2 wherein
- R¹ is hydrogen;
- R² is isopropyl;
- R³ is to yield 3-amino-6-chloro-5-isopropylamino-N-[(2-thiazolinylamino)aminomethylene]-2-pyrazinecarboxamide.

6. A compound of claim 2 wherein
- R¹ is hydrogen;
- R² is hydrogen;
- R³ is

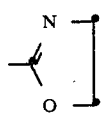

to yield 3,5-diamino-6-chloro-N-[(2-oxazolinylamino)aminomethylene]-2-pyrazinecarboxamide.

7. A compound of claim 2 wherein

R¹ is hydrogen;

R² is hydrogen;

R³ is

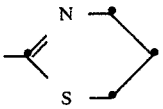

to yield 3,5-diamino-N-[(2-thiazolylamino)aminomethylene]-6-chloro-2-pyrazinecarboxamide.

8. A compound of claim 2 wherein
R¹ is hydrogen;
R² is hydrogen;
R³ is to yield 3,5-diamino-6-chloro-N-{[2-(4,5-dihydro)-thiazinylamino]aminomethylene}-2-pyrazinecarboxamide hydrochloride hemihydrate.

* * * * *